(12) United States Patent
Nakamura

(10) Patent No.: US 9,188,572 B2
(45) Date of Patent: Nov. 17, 2015

(54) LIQUID CHROMATOGRAPHY ANALYZING DEVICE

(71) Applicant: SHIMADZU CORPORATION, Kyoto-shi, Kyoto (JP)

(72) Inventor: Takafumi Nakamura, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 462 days.

(21) Appl. No.: 13/871,863

(22) Filed: Apr. 26, 2013

(65) Prior Publication Data

US 2013/0238254 A1    Sep. 12, 2013

(30) Foreign Application Priority Data

Jan. 7, 2011   (JP) .................................. 2011-002497

(51) Int. Cl.
*G01N 30/86* (2006.01)

(52) U.S. Cl.
CPC ............ *G01N 30/86* (2013.01); *G01N 30/8641* (2013.01); *G01N 30/8658* (2013.01); *G01N 30/8665* (2013.01)

(58) Field of Classification Search
CPC ............ G01N 2030/025; G01N 30/02; G01N 2030/8658; G01N 30/8665
See application file for complete search history.

(56) References Cited

U.S. PATENT DOCUMENTS

| 2007/0271997 | A1* | 11/2007 | O'Brien | G01N 1/2202 73/23.37 |
| 2009/0288473 | A1* | 11/2009 | Suzuki | G01N 30/8665 73/23.41 |
| 2012/0222470 | A1 | 9/2012 | Suzuki et al. | 73/61.56 |

FOREIGN PATENT DOCUMENTS

JP    2009-281897    12/2009

* cited by examiner

*Primary Examiner* — Phuong Huynh
(74) *Attorney, Agent, or Firm* — Morgan, Lewis & Bockius LLP

(57) ABSTRACT

A liquid chromatograph analyzing device, which without an analyst having to set complicated processing conditions before measuring a sample, is able to processes unaffected by fluctuations in room temperature and appearance of ghost peaks. In a liquid chromatograph analyzing device, an automatic sampler, a liquid sending pump, a column oven and a detection device are controlled by a calculation processing device. In addition to chromatograph creation unit, which creates chromatograms of a sample based on input detection signals, the calculation processing device has a correction parameter holding section and correction formula setting unit. The correction formula setting unit provides to the liquid chromatograph analyzing device a functionality for the analyst to set correction formulas for incorporating in the chromatograms created by the chromatograph creation unit changes to environmental conditions such as fluctuations in temperature around the liquid chromatograph analyzing device.

4 Claims, 5 Drawing Sheets

LIQUID CHROMATOGRAPHY ANALYZING DEVICE

TECHNICAL FIELD

The present invention relates to a liquid chromatograph analyzing device equipped with an analysis flow path, sample injection section, separation column, detection device and a computation section.

BACKGROUND ART

A liquid chromatograph analyzing device includes an analysis section comprising an automatic sampler, liquid sending pump, separation column and a detection device, and a computation section comprising, for example, a PC (personal computer). The computation section creates a chromatogram of a measured sample based on detection signals obtained by the detection device (see, for example, Patent Literature 1).

For example, with an analysis based on the temperature gradient method wherein the temperature of the mobile phase is changed with passage of time, because the baseline of the chromatogram drifts with the change in temperature of the mobile phase, background data for a chromatogram is obtained in advance by flowing a blank solution under the same conditions and measuring its chromatogram. As a correction process that is performed after a sample is measured, the background data can be subtracted from the chromatogram data that is obtained by measuring the sample, thus allowing the creation of a chromatogram that is free of the effects of baseline drift caused by a temperature gradient.

Patent Literature 1: Unexamined Patent Application Publication No. 2009-281897

SUMMARY OF THE INVENTION

However, baseline drift can also be caused by fluctuations in temperature (room temperature) that occur during the measurement of a sample where the measurement is being performed. However, current liquid chromatography devices are not constructed so that chromatograms are created taking into account the effects of fluctuations in room temperature that occur during measurement. Furthermore, with the afore-described method of subtracting the background data after measurement data for the sample is obtained, effects of fluctuations in room temperature that occur between the time the background data is obtained and the sample is measured are not accounted for.

Furthermore, with preparative liquid chromatography, separated components are captured based on real-time chromatograms. To explain, this collection method assumes that peaks of a certain level or higher that appear in a chromatogram represent a separate component. When liquid chromatography based on the temperature gradient method is used, the drifting of the baseline of the chromatograms makes it difficult to set a peak level that can be used as a reference for determining whether or not to collect a component. Also, with chromatograms that are created based on detection signals from a detection device, peaks referred to as "ghost peaks," which are peaks that appear in positions unrelated to separated components, are sometimes created. The portions that correspond to such ghost peaks are sometimes erroneously recognized and collected as separated components.

Eliminating the background data with ghost peaks from the measured sample data will eliminate ghost peaks from the chromatogram. However, because this correction process is performed after the measured sample data is collected, this method cannot be used with preparative liquid chromatography wherein separated components are collected based on real-time chromatograms. This meant that avoiding the collection of the portions that correspond to ghost peaks requires performing a blank measurement in advance, forecasting where ghost peaks will appear and setting the device so that portions that correspond to the forecasted ghost peaks are not collected.

It is therefore the object of the present invention to provide a liquid chromatograph analyzing device, which, without requiring the analyst to set complicated processing conditions prior to performing the sample measurement, allows processing to be performed unaffected by room temperature fluctuations and the appearance of ghost peaks.

The present invention is a liquid chromatograph analyzing device including: an analysis flow path through which a mobile phase for transporting a sample flows; a sample injection section for injecting a sample into the analysis flow path; a separation column disposed in the analysis flow path at a position downstream of the sample injection section for separating into individual components a sample that is injected from the sample injection section; a detection device disposed in the analysis flow path at a position further downstream of the separation column for detecting individual components separated by the separation column; a computation section for creating a chromatogram of a sample based on detection signals obtained by the detection device; a correction parameter holding section for holding, as correction parameters, measurement environmental conditions that affect a chromatogram; and a correction formula setting unit for setting correction formulas for reflecting the correction parameters in a chromatogram; wherein: the computation section successively obtains detection signals that are obtained by the detection device and, at the same time, obtains correction parameters corresponding to the detection signals from the correction parameter holding section and successively creates chromatograms that reflect the obtained correction parameters based on the correction formulas that are set by the correction formula setting unit.

If the analyzing device includes a temperature sensor for measuring the surrounding temperature, it is preferable for the correction parameters to include temperature that is obtained by the temperature sensor. By so doing, chromatograms that reflect the effects of fluctuations in room temperature can be created in real-time.

It is also possible for the correction parameters to include background data of the chromatogram that is obtained in advance based on detection signals from the detection device that are obtained by injecting a blank solution into the sample injection section. By so doing, chromatograms from which the background is eliminated can be created in real-time, allowing ghost peaks and drift in baseline caused by a temperature gradient to be eliminated. By applying this method to preparative liquid chromatography, peaks levels to be used for determining whether fractionation will be performed or not can be easily set, preventing the erroneous collection of portions that correspond to ghost peaks.

A liquid chromatograph analyzing device according to the present invention is equipped with a correction parameter holding section for holding measurement environmental conditions that affect chromatograms as correction parameters and correction formula setting unit for setting correction formulas for reflecting the correction parameters in the chromatograms. Furthermore, the computation section is configured so that, as detection signals are obtained from the detection device, correction parameters that correspond to the detection signals are obtained at the same time from the correction parameter holding section and so that chromatograms that reflect the correction parameters that are obtained are successively created based on correction formulas that are set by the correction formula setting unit. This allows chromatograms that are corrected, and thus reflect the correction parameters, to be created in real-time.

DETAILED DESCRIPTION OF THE INVENTION

One embodiment of the liquid chromatograph analyzing device is described next.

Figure 2:
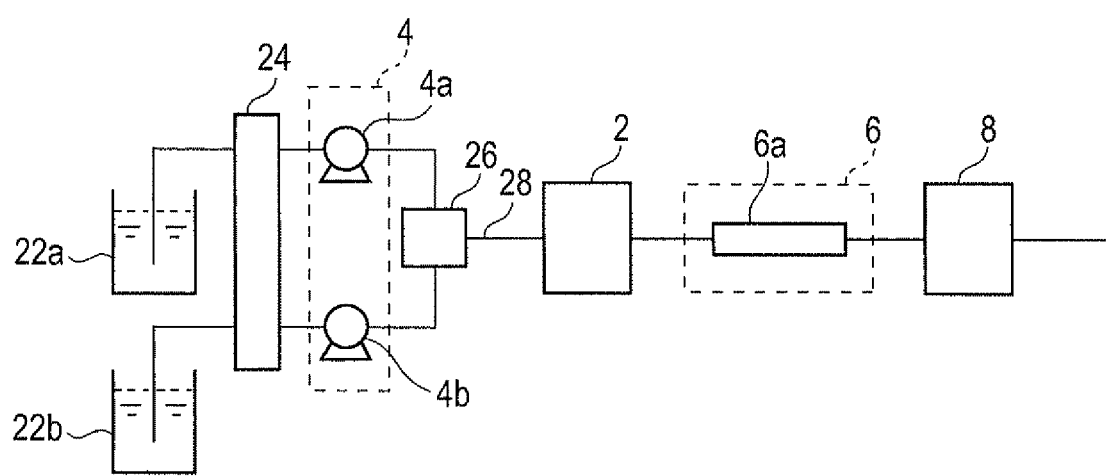
FIG. 2 shows the flow path of the same embodiment.

The flow path of this embodiment is described with reference to FIG. 2.

Connected along analysis flow path 28, starting from the upstream side, are liquid sending pump 4, automatic sampler 2, column oven 6 and detection device 8. The liquid sending pump 4 comprises two pumps, 4a and 4b. The intake side of pump 4a is connected to a container containing mobile phase 22a, and the intake side of pump 4b is connected to a container containing mobile phase 22b, which is different from mobile phase 22a. Each of the connections is made via a degasser 24.

The discharge side of pumps 4a and 4b is connected to mixer 26. Automatic sampler 2 is connected to the downstream side of mixer 26. A sample is injected into analysis flow path 28. Column oven 6, which is connected to the downstream side of automatic sampler 2, is equipped with separation column 6a, which separates the sample that is injected by automatic sampler 2 into individual components. Detection device 8, which is connected to the downstream side of column oven 6, performs optical measurement on the liquid that has passed through separation column 6a. An example of detection device 8 is a differential refractive index detection device.

Figure 1:
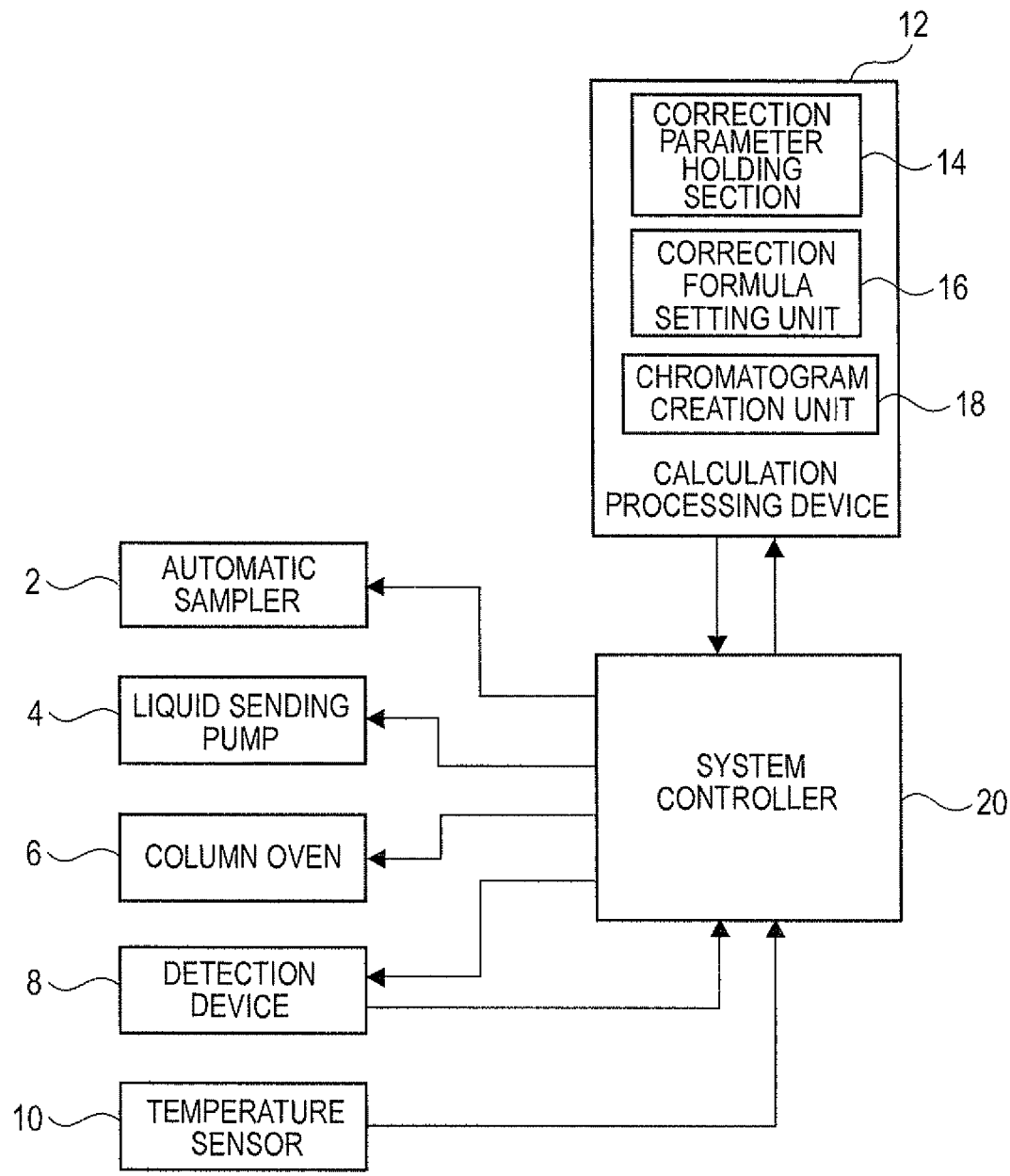
FIG. 1 is a block diagram schematically showing one embodiment of a liquid chromatograph analyzing device.

The control and computation processes that are performed with the afore-described liquid chromatograph analyzing device are described next with reference to FIG. 1. The automatic sampler 2, liquid sending pump 4, column oven 6 and detection device 8 are controlled by calculation processing device 12, which is realized by, for example, a PC serving as the computation section. The analysis conditions are set in the calculation processing device 12. The calculation processing device 12 sends signals that correspond to the set conditions to system controller 20, which then sends control signals that correspond to the set conditions to automatic sampler 2, liquid sending pump 4, column oven 6 and detection device 8. The detection signals that are obtained by detection device 8 are input to calculation processing device 12 via system controller 20. The calculation processing device is equipped with a chromatogram creation unit 18, which creates chromatograms of the samples based on the detection signals that are input.

In addition to the chromatogram creation unit 18, the calculation processing device 12 is equipped with a correction parameter holding section 14 and a correction formula setting unit 16. The correction formula setting unit 16 provides a function to the analyzing device that allows the analyst to set correction formulas, which allow the chromatogram that is created by the chromatogram creation unit 18 to be adjusted to reflect changes in environmental conditions such as fluctuations in ambient temperature around the device.

The purpose of the correction parameter holding section 14 is to hold as correction parameters the measurement environmental conditions that are to be used by the correction formulas set by the analyst using the correction formula setting unit 16 so that the chromatograms reflect the conditions of the measurement environment. Examples of correction parameters that are held in the correction parameter holding section 14 are the temperature around the analyzing device as of when the measurements are taken and background data that are measured in advance by running a blank solution. The temperature around the analyzing device is successively provided via system controller 20 by temperature sensor 10 that is disposed at automatic sampler 2, liquid sending pump 4, column oven 6 or detection device 8.

The chromatogram creation unit 18 successively receives detection signals obtained by detection device 8, while at the same time, obtains correction parameters from the correction parameter holding section 14 and uses the correction formulas that were set by the correction formula setting unit 16 to successively create chromatograms that reflect the correction parameters.

Figure 3:
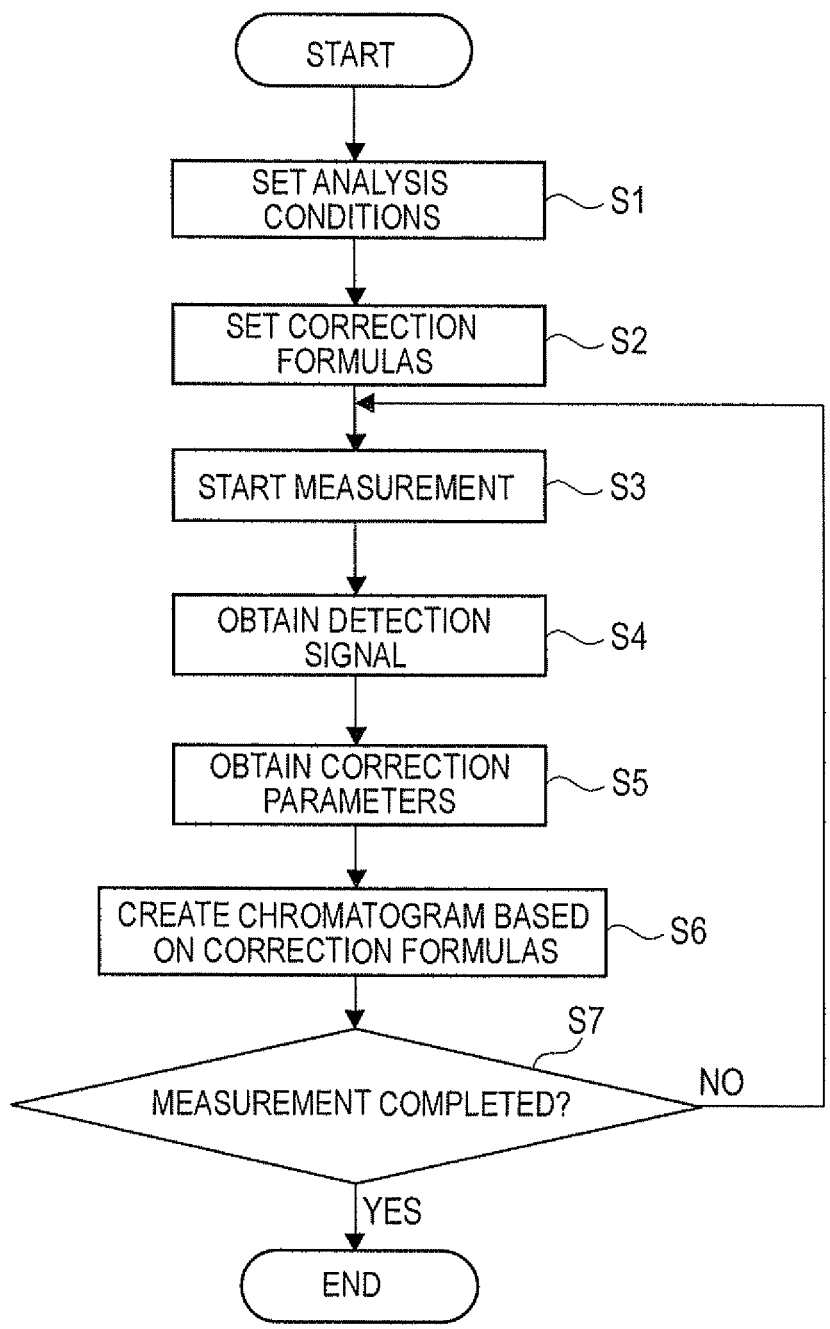
FIG. 3 is a flowchart showing the operation and procedure during measurement by the same embodiment.

The operation and procedure during measurement with the liquid chromatograph analyzing device of the same embodiment are described next with reference to FIG. 3.

First, the analyst sets the analysis conditions such as the flow rate of the mobile phase or the temperature of column oven 6 at the time of measurement (step S1). The analysis conditions that are set here are held as correction parameters by correction parameter holding section 14 of calculation processing device 12.

Next, the correction formula setting unit 16 launches the correction formula setting function, which allows the analyst to set the correction formulas. The analyst can set any correction formula at his option. For example, if the correction that is desired is to subtract the background data (B) that is obtained by measuring a blank solution in advance from the detection signal (C) that is obtained at the time of the measurement, the background data is stored in the correction parameter holding section 14 and the following correction formula is set:

$$X(t)=C(t)-B(t) \quad (1)$$

Here, t is a time variable, and X(t) represents the corrected value of the detection signal at time t, C(t) represents the detection signal measured at time t, and B(t) represents the value of the background data at time t.

Alternately, if the detection device 8 is a differential refractive index detection device, the following correction formula can be set to eliminate the effects of ambient temperature fluctuations on detection device 8 as if the chromatograms were created by measurements obtained at a constant temperature:

$$X(t)=C(t)-K_1 \times T(t) \quad (2)$$

Here, $K_1$ is a correction coefficient (experimental value) for the effect of temperature on the detection signals, and T(t) is the value detected by temperature sensor 10 at time t. To account for delay time ($t_1$) required for the ambient temperature around the device to affect detection device 8, the following correction formula can be set instead of the above correction formula (2):

$$X(t)=C(t)-K_1 \times T(t-t_1) \quad (3)$$

Also, if the measurement is based on the temperature gradient method, the drift in the chromatogram caused by the temperature gradient can be corrected by setting the following correction formula, which uses the temperature profile data (TP) that is set for column oven 6:

$$X(t)=C(t)-K_2 \times TP(t) \quad (4)$$

Here, $K_2$ is a correction coefficient (experimental value) for the effect of column temperature (mobile phase temperature) on the detection signals, and TP(t) is the temperature on the temperature profile at time t.

Also, to account for the heat dissipation from the piping that happens between column oven 6 and detection device 8, the following correction formula is used instead of the above correction formula (4):

$$X(t)=C(t)-K_2 \times (TP(t)-T(t)) \quad (5)$$

Furthermore, to account for time ($t_2$) required for the liquid to reach detection device 8 from column oven 6, the following correction formula is set instead of the above correction formula (5):

$$X(t)=C(t)-K_2 \times (TP(t-t_2)T(t)) \quad (6)$$

Here, $t_2$ is a constant that is determined in advance by the analyst and can be expressed as follows in terms of flow rate (R) of the mobile phase and the volume (L) of the piping from column oven 6 to detection device 8:

$$t_2=L/R \quad (7)$$

This unit that the following correction formula can be set instead of the above correction formula (6):

$$X(t)=C(t)-K_2 \times (TP(t-L/R)-T(t)) \quad (8)$$

The measurement is started after the analyst has set the analysis conditions and the correction formulas for the correction conditions in the afore-described way (step S3). Via the system controller 20, the calculation processing device 18 successively receives detection signal C(t) that is obtained by detection device 8 from the measurement (step S4). At the same time, the calculation processing device 18 also receives the corresponding correction parameters (e.g., B(t), T(t) and TP(t)) from the correction parameter holding section 14 (step S5). The chromatogram creation unit 18 determines the correction value X(t) for the chromatogram based on the detection signal C(t) that it receives and the correction formulas that were set using the correction parameters (step S6). This operation is repeated until the measurement is completed (step S7).

Figure 4A:
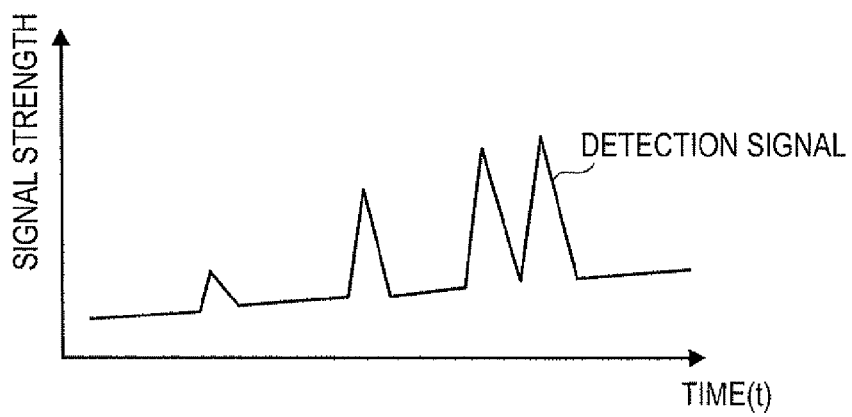
FIG. 4 shows examples of chromatograms. (A) shows the chromatogram before correction, (B) shows the background data of the chromatogram, and (C) shows the chromatogram after correction.
Figure 4B:
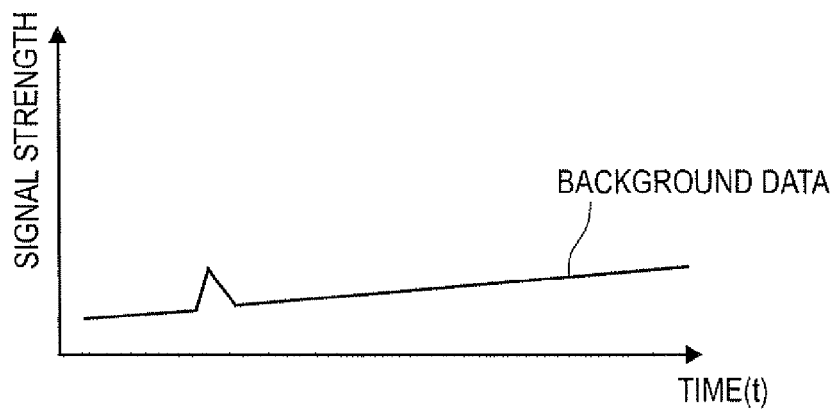
Figure 4C:
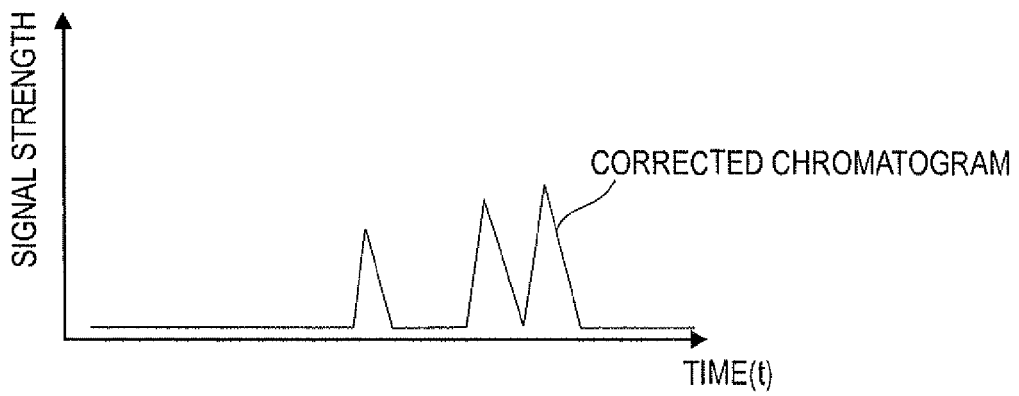
Figure 5:
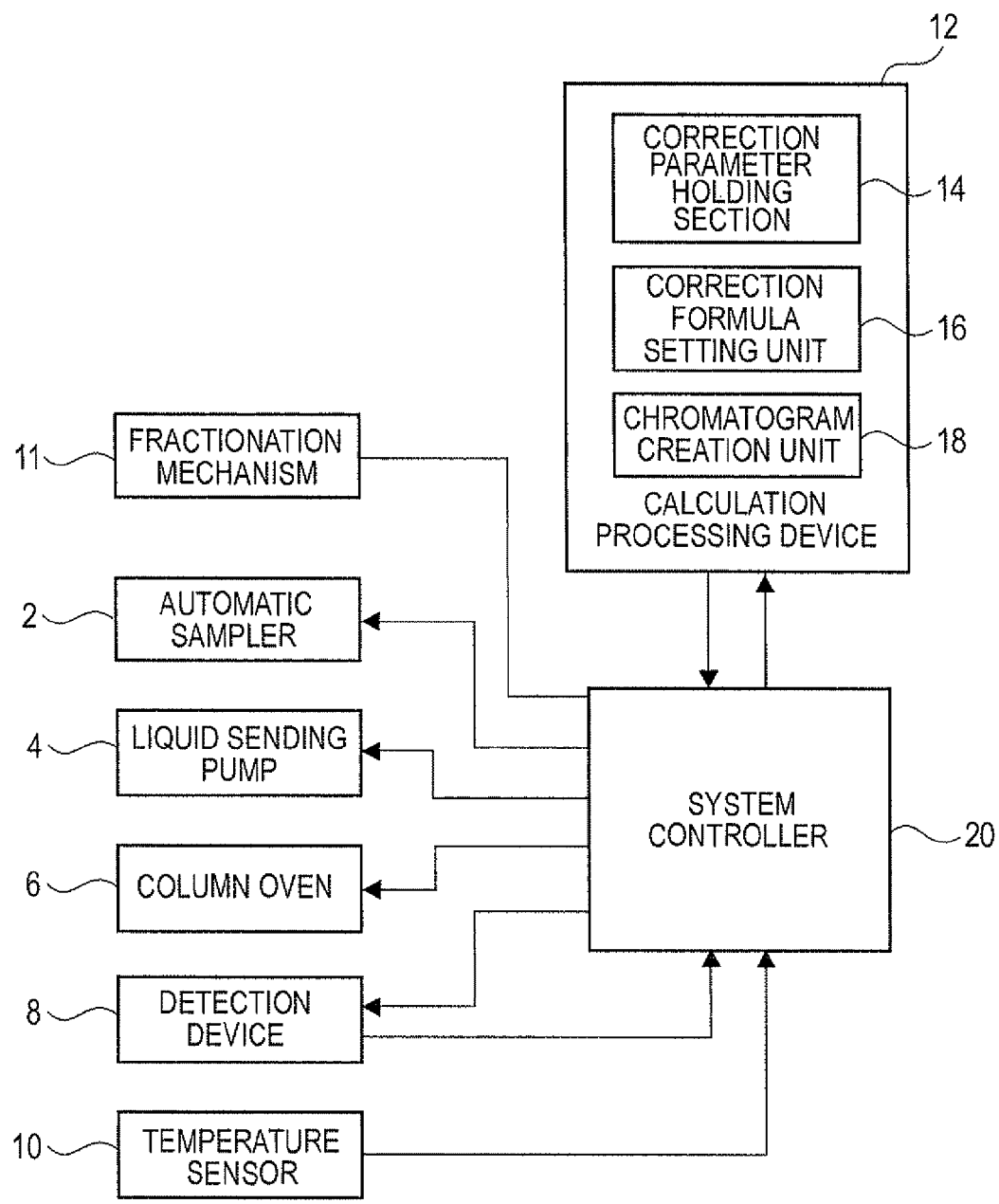
FIG. 5 is a block diagram of one embodiment of a preparative liquid chromatograph, which is an adaptation of a liquid chromatograph analyzing device.

FIG. 4(C) shows an example of a chromatogram that is created using the afore-described operations and procedure. The chromatogram is obtained by subtracting the background data (B) from the detection signal shown in FIG. 4(A). The chromatogram before the correction shown in (A) has drifting of the baseline of the chromatogram caused by temperature gradient and a ghost peak that is unrelated to the sample components. However, by subtracting the background data (B), the ghost peak and the drift caused by the temperature gradient are eliminated to provide a chromatogram in real-time whose baseline is constant. By obtaining such chromatogram in real-time, with a preparative liquid chromatograph equipped with a fractionation mechanism 11 that fractionates sample components that are discharged from the downstream end of the analysis flow path based on a chromatogram such as that shown in FIG. 5, signal strength levels used as a reference for determining whether to fractionate or not can be easily set, and erroneous fractionation of components that correspond to ghost peaks is eliminated.

Even though, with the afore-described embodiment, the correction parameter holding section 14 was provided in the calculation processing device 12, the correction parameter holding section 14 can also be provided in system controller 20. In fact, the correction parameter holding section 14 can be disposed at any position so long as data that is used as correction parameters for chromatograms such as data from temperature sensor 10 can be collected.

Furthermore, even though, with the afore-described embodiment, the analyzing device that is described was configured so that elements such as the automatic sampler 2 and the liquid sending pump were controlled via system controller 20, the present invention can be similarly used with an analyzing device wherein system controller 20 is not provided, and the individual elements are directly controlled by calculation processing device 12.

LEGEND

2. Automatic sampler
4. Liquid sending pump
6. Column oven
6a. Analysis column
8. Detection device
10. Temperature sensor
12. Calculation processing device
14. Correction parameter holding section
16. Correction formula setting unit
18. Chromatogram creation unit
20. System controller
24. Degasser
26. Mixer
28. Analysis flow path

What is claimed is:

1. A liquid chromatograph analyzing device comprising:
    an analysis flow path through which a mobile phase for transporting a sample flows;
    a sample injection section for injecting a sample into said analysis flow path;
    a separation column disposed in said analysis flow path at a position downstream of said sample injection section and for separating into individual components a sample that is injected from said sample injection section;
    a detection device disposed in said analysis flow path at a position further downstream of said separation column and for detecting individual components separated by said separation column;
    a computation section for creating a chromatogram of a sample based on detection signals obtained by said detection device;
    a correction parameter holding section for holding, as correction parameters, measurement environmental conditions that affect a chromatogram; and
    a correction formula setting unit for setting correction formulas for reflecting said correction parameters in a chromatogram;
    wherein:
    said computation section successively obtains detection signals that are obtained by said detection device and, at the same time, obtains correction parameters corresponding to said detection signals from said correction parameter holding section and successively creates chromatograms that reflect the obtained correction parameters based on the correction formulas that are set by said correction formula setting unit.

2. The liquid chromatograph analyzing device according to claim 1 further comprising a temperature sensor for measuring the temperature around said liquid chromatograph analyzing device wherein said correction parameters further includes temperature obtained by said temperature sensor.

3. The liquid chromatograph analyzing device according to claim 1 or claim 2 wherein said correction parameters are background data of the chromatogram obtained by measuring in advance the detection signal from said detection device upon injection of a blank solution into said sample injection section.

4. The liquid chromatograph analyzing device according to claim 3 further comprising a fractionation mechanism disposed at the downstream end of said analysis flow path for collecting liquid coming from said analysis flow path wherein said fractionation mechanism fractions and captures portions that correspond to the separated components based on a chromatogram that reflect said background data as a correction parameter.

\* \* \* \* \*